United States Patent [19]
Forbes et al.

[11] Patent Number: 5,508,288
[45] Date of Patent: Apr. 16, 1996

[54] INDOLE DERIVATIVES AS 5HT$_{1C}$ ANTAGONISTS

[75] Inventors: Ian T. Forbes, Stevenage; Roger T. Martin, Ware; Graham E. Jones, Hertford, all of England

[73] Assignee: SmithKline Beecham, p.l.c., United Kingdom

[21] Appl. No.: 295,694

[22] PCT Filed: Mar. 4, 1993

[86] PCT No.: PCT/GB93/00449

§ 371 Date: Aug. 30, 1994

§ 102(e) Date: Aug. 30, 1994

[87] PCT Pub. No.: WO93/18028

PCT Pub. Date: Sep. 16, 1993

[30] Foreign Application Priority Data

Mar. 12, 1992 [GB] United Kingdom ............ 9205415
Mar. 12, 1992 [GB] United Kingdom ............ 9205416
Mar. 12, 1992 [GB] United Kingdom ............ 9205422
Mar. 12, 1992 [GB] United Kingdom ............ 9205442

[51] Int. Cl.⁶ .................... A61K 31/475; C07D 401/04
[52] U.S. Cl. ................ 514/310; 514/314; 546/143; 546/163
[58] Field of Search ................ 546/143, 163; 514/310, 314

[56] References Cited

FOREIGN PATENT DOCUMENTS

WO92/05170  4/1992  WIPO.

OTHER PUBLICATIONS

Fludzinski, et al., "2,3-Dialkyl(dimethylamino)indoles: Interaction with 5HT$_1$, 5HT$_2$, and Rat Stomach Fundal Serotonin Receptors", *J. Med. Chem.* 29: 2415–2418 (1986).

*Primary Examiner*—C. Warren Ivy
*Assistant Examiner*—Evelyn Huang
*Attorney, Agent, or Firm*—Linda E. Hall; Stuart R. Suter; Edward T. Lentz

[57] ABSTRACT

A compound of formula (I) or a salt thereof:

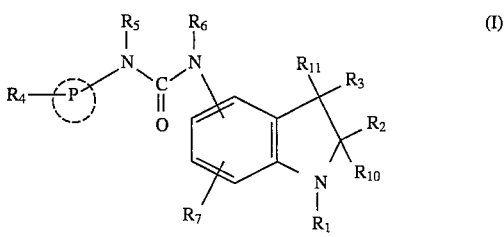

Wherein:

P represents a quinoline or isoquinoline residue; $R_1$ is hydrogen or $C_{1-6}$ alkyl; $R_2$, $R_3$, $R_{10}$, $R_{11}$ are independently hydrogen $R_1$ is hydrogen or $C_{1-6}$ alkyl; $R_2$, $R_3$, $R_{10}$, $R_{11}$ are independently hydrogen or $C_{1-6}$ alkyl, or $R_{10}$ and $R_{11}$ together form a bond, or $R_2$ and $R_{10}$ or $R_3$ and $R_{11}$ together form a $C_{2-6}$ alkylene chain. $R_4$ is hydrogen, $C_{1-6}$ alkyl, halogen, $NR_8R_9$, $OR_{12}$ or $COOR_{12}$, where $R_8R_9$ and $R_{12}$ are independently hydrogen or $C_{1-6}$ alkyl; $R_5$ and $R_6$ are independently hydrogen or $C_{1-6}$ alkyl; and $R_7$ is hydrogen, $C_{1-6}$ alkyl, $C_{1-6}$ alkoxy or halogen; and wherein the urea moiety is attached at the 4-, 5- or 6-position of the indoline ring, which has been found to have 5HT$_{1c}$ receptor antagonist activity.

9 Claims, No Drawings

INDOLE DERIVATIVES AS 5HT$_{1C}$ ANTAGONISTS

This application is the National Phase of PCT/GB93/00449 filed on Mar. 4, 1993.

This invention relates to compounds having pharmacological activity, to a process for their preparation, to compositions containing them and to their use in the treatment of mammals.

P. Fludzinski et al. J. Med. Chem. 1986 29 2415–2418 describes N-(1,2-dimethyl-3-ethyl-1H-indol-5-yl)-N'-(3-trifluoromethylphenyl)urea which shows selectivity for the rat stomach fundus seretonin receptor.

A class of compounds has now been discovered which have been found to have 5HT$_{1C}$ receptor antagonist activity. 5HT$_{1C}$ receptor antagonists are believed to be of potential use in the treatment of CNS disorders such as anxiety, depression, obsessive compulsive disorders, migraine, anorexia, Alzheimers disease, sleep disorders, bulimia, panic attacks, withdrawal from drug abuse such as cocaine, ethanol, nicotine, and benzodiazepines, schizophrenia, and also disorders associated with spinal trauma and/or head injury, such as hydrocephalus.

Accordingly, the present invention provides a compound of formula (I) or a salt thereof:

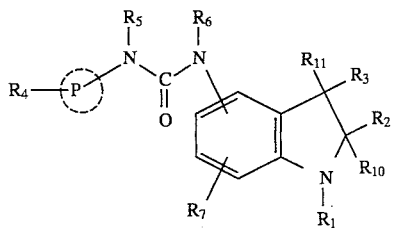

wherein:

P represents a quinoline or isoquinoline residue or a 5- or 6-membered aromatic heterocyclic ring containing up to three heteroatoms selected from nitrogen, oxygen or sulphur;

$R_1$ is hydrogen or $C_{1-6}$ alkyl;

$R_2$, $R_3$, $R_{10}$ and $R_{11}$ are independently hydrogen or $C_{1-6}$ alkyl, or $R_{10}$ and $R_{11}$ together form a bond, or $R_2$ and $R_{10}$ or $R_3$ and $R_{11}$ together form a $C_{2-6}$ alkylene chain;

$R_4$ is hydrogen, $C_{1-6}$ alkyl, halogen, $NR_8R_9$, $OR_{12}$ or $COOR_{12}$, where $R_8$, $R_9$ and $R_{12}$ are independently hydrogen or $C_{1-6}$ alkyl;

$R_5$ and $R_6$ are independently hydrogen or $C_{1-6}$ alkyl; and $R_7$ is hydrogen, $C_{1-6}$ alkyl, $C_{1-6}$ alkoxy or halogen; and wherein the urea moiety is attached at the 4-, 5- or 6-position of the indole or indoline ring, provided that P is not pyridyl when $R_{10}$ and $R_{11}$ form a bond.

Alkyl moieties within the variables $R_1$ to $R_{12}$ are preferably $C_{1-3}$ alkyl, such as methyl, ethyl, n- and iso-propyl, most preferably methyl.

Suitable $R_4$ and $R_7$ halogens include chloro and bromo.

Examples of $R_1$ include hydrogen, methyl, ethyl and n-propyl, preferably methyl.

$R_2$ and $R_3$ are preferably hydrogen. $R_{10}$ and $R_{11}$ are preferably a bond so as to form an indole structure. In an indoline structure, $R_{10}$ and $R_{11}$ are preferably hydrogen.

Preferably $R_4$ is hydrogen or methyl, most preferably hydrogen.

Preferably $R_5$, $R_6$ and $R_7$ are hydrogen.

The urea moiety can be attached to a carbon or nitrogen atom of the ring P, preferably it is attached to a carbon atom.

Suitable moieties when the ring P is a 5- or 6-membered aromatic heterocyclic ring include pyrazinyl, pyridazinyl, pyrimidinyl, isothiazolyl, isoxazolyl, thiadiazolyl and triazolyl. When P is a quinoline or isoquinoline residue, the urea moiety can be attached at any position of the ring, preferably to the 4-position.

The urea moiety is preferably attached at the 5-position of the indole or indoline ring.

The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulphonic acids.

Compounds of formula (I) may also form N-oxides or solvates such as hydrates, and the invention also extends to these forms. When referred to herein, it is understood that the term compound of formula (I) also includes these forms.

When $R_1$ (in an indole) and/or $R_5$ and/or $R_6$ are hydrogen or when $R_4$ is hydroxy or $NR_8R_9$ and at least one of $R_8$ and $R_9$ are hydrogen the compounds of formula (I) may exist tautomerically in more than one form. The invention extends to these and any other tautomeric forms and mixtures thereof.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis.

The present invention also provides a process for the preparation of a compound of formula (I) or a pharmaceutically acceptable salt thereof, which process comprises:

(a) the coupling of a compound of formula (II);

with a compound of formula (III);

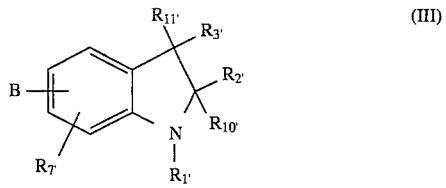

wherein B is attached at the 4-, 5- or 6-position of the indole or indoline ring and A and B contain the appropriate functional group(s) necessary to form the moiety —NR$_5$'CONR$_6$'— when coupled, wherein $R_5$' and $R_6$' are $R_5$ and $R_6$ as defined in formula (I) or groups convertible thereto, and the variables $R_1$', $R_2$', $R_3$', $R_{10}$', $R_{11}$', $R_4$' and $R_7$' are $R_1$, $R_2$, $R_3$, $R_{10}$, $R_{11}$, $R_4$ and $R_7$ respectively, as defined in formula (I), or groups convertible thereto, and thereafter optionally and as necessary and in any appropriate order, converting any $R_1$', $R_2$', $R_3$', $R_{10}$', $R_{11}$', $R_4$', $R_5$', $R_6$' and $R_7$' when other than $R_1$, $R_2$, $R_3$, $R_{10}$, $R_{11}$, $R_4$, $R_5$, $R_6$ and $R_7$ respectively to $R_1$, $R_2$, $R_3$, $R_{10}$, $R_{11}$, $R_4$, $R_5$, $R_6$ and $R_7$, interconverting $R_1$, $R_2$, $R_3$, $R_{10}$, $R_{11}$, $R_4$, $R_5$, $R_6$ and $R_7$, and forming a pharmaceutically acceptable salt thereof; or (b) cyclising a compound of formula (IV):

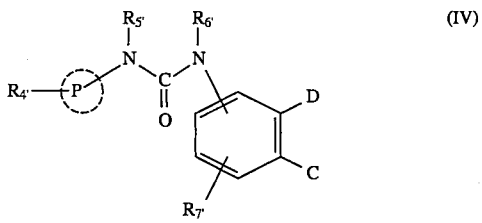

(IV)

wherein $R_4'$, $R_5'$, $R_6'$ and $R_7'$ are as defined in formulae (II) and (III) and C and D contain the appropriate functional group(s) necessary to form the indole or indoline ring substituted by $R_1'$, $R_2'$, $R_3'$, $R_{10}'$, and $R_{11}'$ as defined in formula (III), and thereafter optionally and as necessary in any appropriate order, converting any $R_1'$, $R_2'$, $R_3'$, $R_{10}'$, $R_{11}'$, $R_4'$, $R_5'$, $R_6'$ and $R_7'$ when other than $R_1$, $R_2$, $R_3$, $R_{10}$, $R_{11}$, $R_4$, $R_5$, $R_6$ and $R_7$, to $R_1$, $R_2$, $R_3$, $R_{10}$, $R_{11}$, $R_4$, $R_5$, $R_6$ and $R_7$, interconverting $R_1$, $R_2$, $R_3$, $R_{10}$, $R_{11}$, $R_4$, $R_5$, $R_6$ and $R_7$, and optionally thereafter forming a pharmaceutically acceptable salt.

Suitable examples of groups A and B include:

(i) A is —N=C=O and B is —$NHR_6'$, (ii) A is —$NHR_5'$ and B is —N=C=O, (iii) A is —$NR_5'COL$ and B is —$NHR_6'$, (iv) A is —$NHR_5'$ and B is —$NR_6'COL$, or (v) A is halogen and B is —$NR_6'CONHR_5'$, wherein $R_5'$ and $R_6'$ are as defined above and L is a leaving group. Examples of suitable leaving groups L include halogen such as chloro or bromo, imidazole, or phenoxy or phenylthio optionally substituted for example with halogen.

When A is —N=C=O and B is $NHR_6'$ or when A is $NHR_5'$ and B is —N=C=O the reaction is suitably carried out in an inert solvent for example dichloromethane or toluene at ambient temperature.

When A is —$NR_5'COL$ and B is —$NHR_6'$ or when A is —$NHR_5'$ and B is —$NR_6'COL$, the reaction is suitably carried out in an inert solvent such as dichloromethane at ambient temperature optionally in the presence of a base, such as triethylamine or in dimethylformamide at ambient or elevated temperature.

When A is halogen and B is —$NR_6'CONHR_5'$, the reaction is suitably carried out in an inert solvent such as toluene at elevated temperature, optionally in the presence of a base.

The cyclisation of the compound of formula (IV) to prepare indoles ($R_{10}$ and $R_{11}$ are a bond) may be effected using standard methodology such as described in Comprehensive Heterocyclic Chemistry 1984 4, 313 et seq. or J. Het. Chem. 1988 25 p.1 et seq.

Examples of the more important routes include the Leimgruber synthesis, the Fischer synthesis and the Japp-Klingemann variation and the Madelung synthesis.

Examples of the groups C and D in the preparation of indoles include:

(vi) C is $NO_2$ and D is CH=CH—$NZ_2$ where each Z is independently $C_{1-6}$ alkyl or together represent $C_{2-7}$ alkylene;

(vii) C is $NR_1'$—N=$C(R_2')$—$CH_2R_3'$ and D is H;

(viii) C is NH—N=$C(CO_2X)$—$CH_2R_3'$ and D is H where X is $C_{1-6}$ alkyl; and (ix) C is $NR_1'COR_2'$ and D is $CH_2R_3'$.

The preparation of indolines includes:

(x) C is $NHR_1'$ and D is $C(R_3')(R_{11}')C(R_2')(R_{10}')L$ where L is a leaving group.

Indolines may also be prepared by reduction, e.g. with $NaCNBH_3$, of indoles produced by variants (vi) to (ix) above.

In reaction variant (vi) (Leimgruber synthesis) the compound of formula (IV) is prepared from the 2-methylnitrophenyl urea by treatment with a dialkylacetal of the dialkylformamide $OHCNZ_2$ with heating and the product of formula (IV) cyclised by hydrogenation over a suitable catalyst such as palladium and charcoal optionally under pressure to yield the compound of formula (I) where $R_1=R_2=R_3=H$.

In reaction variant (vii) (Fischer synthesis) the compound of formula (IV) is prepared from the hydrazinophenyl urea by dehydration, preferably by heating, with the appropriate ketone $R_2'COCH_2R_3'$ and the product of formula (IV) cyclised by heating with an acid catalyst such as hydrochloric or sulphuric acid.

In reaction variant (viii) (Japp-Klingemann synthesis) the compound of formula (IV) is prepared from the aminophenyl urea by diazotisation followed by treatment for example with $CH_3COCH(CO_2X)$—$CH_2R_3'$ where X is $C_{1-6}$ alkyl under basic conditions in aqueous alcohol as solvent.

The product of formula (IV) my then be cyclised as in the Fischer synthesis above.

In reaction variant (ix) (Madelung synthesis) the compound of formula (IV) is cyclised with base in an inert solvent optionally with heating.

In reaction variant (x), the compound of formula (IV) is cyclised by heating in an inert solvent, optionally in the presence of a base.

It will be appreciated that when D is hydrogen, either or both indole isomers may be formed during the cyclisation process.

Suitable examples of groups $R_2'$, $R_3'$, $R_4'$, and $R_7'$ which are convertible to $R_2$, $R_3$, $R_4$, and $R_7$ alkyl groups respectively, include acyl groups which are introduced conventionally and may be converted to the corresponding alkyl group by conventional reduction, such as using sodium borohydride in an inert solvent followed by hydrogenolysis in an inert solvent. Hydrogen substituents may be obtained from alkoxycarbonyl groups which may be converted to hydrogen by hydrolysis and decarboxylation. When $R_4$ is hydroxy it is preferably protected in the compound of formula (II) as, for example, benzyl which is removed by hydrogenation.

Suitable examples of a group $R_1'$ which is convertible to $R_1$, include typical N-protecting groups such as alkoxycarbonyl, in particular t-butyloxycarbonyl, acetyl, trifluoroacetyl, benzyl and para-methoxybenzyl which are converted to $R_1$ hydrogen using conventional conditions.

Suitable examples of groups $R_5'$ and $R_6'$ which are convertible to $R_5$ and $R_6$ respectively include alkoxycarbonyl and benzyl or para-methoxybenzyl which are converted to $R_5$ and/or $R_6$ hydrogen using conventional conditions.

Interconversions of $R_1$, $R_2$, $R_3$, $R_{10}$, $R_{11}$, $R_4$, $R_5$, $R_6$ and $R_7$ are carried out by conventional procedures.

For example, in the case wherein $R_1$, $R_2$ and $R_3$ are $C_{1-6}$ alkyl and $R_5$ and $R_6$ are hydrogen it is possible to introduce a $C_{1-6}$ alkyl group at both the $R_5$ and $R_6$ positions by conventional alkylation using 2 molar equivalents of a $C_{1-6}$ alkyl halide and 2 molar equivalents of a suitable base in an inert solvent. Monoalkylation can be achieved using 1 molar equivalent of a $C_{1-6}$ alkyl halide and base using conventional conditions. $R_1$ $C_{1-6}$ alkyl groups may also be introduced by conventional alkylation, for example using a $C_{1-6}$ alkyl halide and base such as sodium hydride, or by reduction of $C_{1-6}$ acyl.

$R_4$ halo and $R_7$ halo may be introduced by selective halogenation of the ring P or indole/indoline ring respectively using conventional conditions.

It should be appreciated that it may be necessary to protect any $R_1$ to $R_{12}$ hydrogen variables which are not required to be interconverted.

Protection, especially of a $R_1'$ hydrogen, may also be necessary during coupling reaction (a) and ring-forming reaction (b) above.

Suitable protecting groups and methods for their attachment and removal are conventional in the art of organic chemistry, such as those described in Greene T. W. 'Protective groups in organic synthesis' New York, Wiley (1981).

It is preferable, however, to introduce and interconvert the groups $R_1$ to $R_{12}$ before coupling compounds of formulae (II) and (III) together, or cyclising the compound of formula (IV).

Compounds of formula (I) which are substituted indoles, and their appropriate derivatives, can be converted to the corresponding indolines, and vice versa, by conventional methods, e.g. reduction with $NaCNBH_3$ in acetic acid and oxidation using $MnO_2$ in an inert solvent.

Compounds of formula (II) in which A is $NHR_5'$ are known compounds or can be prepared analogously to known compounds.

For example, aminopyrazine and 4-aminoquinaldine are commercially available from Aldrich, and 3-amino-6-chloro-pyridazine is commercially available from Lancaster.

Compounds of formula (II) in which A is —N═C═O may be prepared by treating a compound of formula (II) in which:

i) A is amino, with phosgene or a phosgene equivalent, in the presence of excess base in an inert solvent.

ii) A is acylazide (i.e. $CON_3$), via the nitrene, by thermal rearrangement using conventional conditions (ref L. S. Trifonov et al., Helv. Chim. Acta 1987 70 262).

iii) A is $CONH_2$, via the nitrene intermediate using conventional conditions.

Compounds of formula (II) in which A is —$NR_5'COL$ may be prepared by reacting a compound of formula (II) in which A is —$NHR_5'$ with phosgene or a phosgene equivalent, in an inert solvent, at low temperature, if necessary in the presence of one equivalent of a base such as triethylamine.

Compounds of formula (II) in which A is halogen and $R_4'$ is hydrogen are commercially available.

Compounds of formula (III) in which B is $NHR_6'$ are known compounds or can be prepared analogously to known compounds, for example by reduction of the corresponding nitroindole or nitroindoline by catalytic hydrogenation over Pd/C by the method of P. Fludzinski et al. J. Med. Chem., 1986, 29 2415. Specifically, the compound of formula (III) in which $R_1'$ and $R_2'$ are methyl, $R_3'$ is ethyl, $R_{10}'$ and $R_{11}'$ are a bond, $R_6'$ and $R_7'$ are hydrogen and B is $NH_2$ is prepared using a procedure similar to that described by Fludzinski.

The nitroindoles and nitroindolines are commercially available, for example 5-nitroindole and 5-nitroindoline, or may be prepared conventionally (Comprehensive Heterocyclic Chemistry Vol. 4 p. 313 et seq. (Pergamon Press 1984) and J. Het. Chem. 1988 25 p.1 et seq.)

An $R_2'$ alkoxycarbonyl group may be eliminated to give $R_2'$ hydrogen, generally under the conditions effecting formation of the nitroindole or as a subsequent step in the process.

$R_6'$ alkyl groups may be introduced conventionally, for example by reductive alkylation or acylation and reduction. $R_7'$ $C_{1-6}$ alkyl groups may be introduced ortho to a nitro substituent by alkylation using a procedure similar to that described in G. Bartoli et al., J. Org. Chem. 1986 51 3694 and Tetrahedron 1987 43 4221.

Compounds of formula (III) in which B is —N═C═O may be prepared by treating a compound of formula (III) in which:

i) B is amino, with phosgene or a phosgene equivalent, in the presence of excess base in an inert solvent.

ii) B is acylazide (i.e. $CON_3$), via the nitrene, by thermal rearrangement using conventional conditions.

iii) B is $CONH_2$, via the nitrene intermediate using conventional conditions.

Compounds of formula (III) in which B is —$NR_6'COL$ may be prepared by reacting a compound of formula (III) in which B is —$NHR_6'$ with phosgene or a phosgene equivalent, in an inert solvent, at low temperature, if necessary in the presence of one equivalent of a base such as triethylamine.

Compounds of formula (III) in which B is —$NR_6'CONHR_5'$ can be prepared from the corresponding precursor where B is $NHR_6'$ by reaction with an $R_5'$ isocyanate under conventional conditions.

Examples of phosgene equivalents include triphosgene, carbonyldiimidazole, phenyl chloroformate and phenyl chlorothioformate.

Novel intermediates of formula (III) also form part of the invention.

Compounds of formula (IV) may be prepared from the appropriate aminophenyl derivative analogously to compounds of formula (I).

Novel intermediates of formula (IV) also form part of the invention.

Pharmaceutically acceptable salts may be prepared conventionally by reaction with the appropriate acid or acid derivative.

N-oxides may be formed conventionally by reaction with hydrogen peroxide or percarboxylic acids.

Compounds of formula (I) and their pharmaceutically acceptable salts have $5HT_{1C}$ receptor antagonist activity and are believed to be of potential use in the treatment or prophylaxis of anxiety, depression, migraine, anorexia, obsessive compulsive disorders, Alzheimer's disease, sleep disorders, bullmia, panic attacks, withdrawal from drug abuse such as cocaine, ethanol, nicone, and benzodiazepines, schizophrenia, and also disorders associated with spinal trauma and/or head injuries, such as hydrocephalus.

Thus the invention also provides a compound of formula (I) or a pharmaceutically acceptable salt thereof, for use as a therapeutic substance, in particular in the treatment or prophylaxis of anxiety, depression, migraine, anorexia, obsessive compulsive disorders, Alzheimer's disease, sleep disorders, bulimia, panic attacks, withdrawal from drug abuse such as cocaine, ethanol, nicotine, and benzodiazepines, schizophrenia, and also disorders associated with spinal trauma and/or head injuries, such as hydrocephalus.

The invention further provides a method of treatment or prophylaxis of anxiety, depression, migraine, anorexia, obsessive compulsive disorders, Alzheimer's disease, sleep disorders, bulimia, panic attacks, withdrawal from drug abuse such as cocaine, ethanol, nicotine, and benzodiazepines, schizophrenia, and also disorders associated with spinal trauma and/or head injuries, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for the treatment or prophylaxis of anxiety, depression, migraine, anorexia, obsessive compulsive disorders, Alzheimer's disease, sleep disorders, bulimia, panic attacks, withdrawal from drug abuse such as cocaine, ethanol, nicotine, and benzodiazepines, schizophrenia, and also disorders associated with spinal trauma and/or head injuries.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorder will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.01 to 100 mg/kg; and such therapy may extend for a number of weeks or months.

When administered in accordance with the invention, no unacceptable toxicological effects are expected with the compounds of the invention.

The following Examples illustrate the preparation of pharmacologically active compounds of the invention. The following Descriptions illustrate the preparation of intermediates to compounds of the present invention.

Description 1

1-Methyl-5-nitro-1H-indole (D1)

To a stirred suspension of sodium hydride (5.0 g; 167 mmol) in dimethylformamide (200 ml) at 0° C. under nitrogen was added 5-nitroindole (25 g; 154 mmol) in dimethylformamide. After stirring for 0.5 h, iodomethane (10.5 ml; 168 mmol) in dimethylformamide (50 ml) was added, and stirring was continued for 2 h. The reaction mixture was then quenched with water, and poured onto excess water with stirring. Filtration afforded the title compound (27.4 g; 94%).

NMR (CDCl$_{13}$) δ: 3.88 (3H, s), 6.68 (1H, d, J=3), 7.21 (1H, d, J=3), 7.34 (1H, d, J=8, 8.13 (1H, dd, J=8, 2), 8.59 (1H, d, J=2).

Description 2

5-Amino-1-methyl-1H-indole (D2)

A mixture of the nitroindole (D1) (5 g; 28.4 mmol) and 5% palladium on charcoal in ethanol (300 ml) was hydrogenated at 60 p.s.i. (4.14×10$^5$Pa) at room temperature for 3 h. Removal of the catalyst by filtration followed by evaporation of the solvent gave the title compound (3.39 g, 95%).

NMR (CDCl$_3$) δ: 3.20 (2H, broad s), 3.70 (3H, s), 6.28 (1H, d, J=3), 6.68 (1H, dd, J=8, 2), 6.92 (1H, d, J=2), 6.96 (1H, d, J=3), 7.12 (1H, d, J=8).

Description 3

Phenyl N-(1-Methyl-1H-indol-5-yl) carbamate (D3)

To a solution of phenyl chloroformate (2.21 ml; 17.4 mmol) in dry tetrahydrofuran (30 ml), cooled in a carbon tetrachloride/solid carbon dioxide bath, was added 5-amino-1-methylindole (D2) (2.31 g; 15.8 mmol) followed by triethylamine (2.40 ml; 17.4 mmol). The mixture was stirred for 45 min at −20° C. (bath temperature), then evaporated. The residue was dissolved in ethyl acetate, washed with brine, dried and evaporated to give the title compound (4.29 g; 100%), m.p. 103°–107° C. (EtOAc/petrol).

NMR (CDCl$_3$) δ: 3.80 (3H, s), 6.45 (1H, d, J=3), 6.93 (1H, broad s), 7.05 (1H, d, J=3), 7.25 (5H, m), 7.40 (2H, dd, J=8, 8), 7.74 (1H, broad s).

Description 4

Pyrimidine-5-carboxylic acid (D4)

n-Butyllithium (1.6M in hexane, 6.9 ml, 11 mmol) was added to dry THF (10 ml) and the solution was cooled to −100° C. A solution of 5-bromopyrimidine (1.59 g, 10 mmol) in dry THF (50 ml) was added slowly. After 15 min at −80° to −100° C., the mixture was added dropwise onto solid carbon dioxide in dry THF. After warming to room temperature, the mixture was made slightly acidic with dilute sulphuric acid. The solid was filtered off and extracted with ethanol. The extract was filtered and evaporated and the residue was re-extracted with methanol. Evaporation of solvent gave the title compound (1.48 g, 100%).

NMR (d$_4$-MeOH) δ: 9.17 (1H, s), 9.20 (2H, s). m/z (EI): 124 (M$^+$)

Example 1

N-(1-Methyl-5-indolyl)-N'-(2-pyrazinyl) urea (E1)

To a suspension of sodium hydride (80% in oil, 0.66 g, 22 mmol) in dry DMF (50 ml) was added 2-aminopyrazine (0.95 g, 10 mmol). After hydrogen evolution had ceased (15 min), phenyl N-(1-methyl-5-indolyl) carbamate (D3) (2.67 g, 10 mmol) was added, followed by a further portion of sodium hydride (0.2 g). The mixture was stirred overnight at room temperature and then evaporated in vacuo. The residue was dissolved in dichloromethane/methanol and washed with water and brine. The organic phase was dried and evaporated and the residue was triturated with dichloromethane/petrol. The residue was then recrystallised from DMSO/water to give the title compound (1.09 g). m.p. 222°–226° C.

Found: C, 62.75; H, 4.83; N, 26.10 $C_{14}H_{13}N_5O$ requires: C, 62.91; H, 4.90; N, 26.20% NMR ($D_6$-DMSO) δ: 3.78 (3H, s), 6.38 (1H, d, J=3), 7.19 (1H, dd, J=8, 2), 7.30 (1H, d, J=3), 7.38 (1H, d, J=8), 7.77 (1H, d, J=2), 8.22 (1H, d, J=2), 8.30 (1H, m), 9.01 (1H, s), 9.52 (1H, s), 9.57 (1H, s).

Example 2

N-(1-Methyl-5-indolyl)-N'-(3-pyridazinyl) urea (E2)

The title compound (0.53 g) was prepared by the method of Example 1, using sodium hydride (0.59 g, 19.7 mmol), 3-aminopyridazine (0.85 g, 8.95 mmol) and carbamate (D3) (2.39 g, 8.95 mmol) in DMF (40 ml). mp. 220°–225° C., 96.5% pure by HPLC.

NMR ($d_6$-DMSO) δ: 3.78 (3H, s), 6.38 (1H, d, J=3), 7.18 (1H, dd, J=8, 2), 7.30 (1H, d, J=3), 7.39 (1H, d, J=8), 7.72 (1H, dd, J=5, 9), 7.75 (1H, d, J=2), 8.0 (1H, d, J=9), 8.85 (1H, d, J=5), 9.69 (1H, s), 9.73 (1H, s). m/z (EI): 267 ($M^+$), 172, 146.

Example 3

N-(1-Methyl-5-indolyl)-N'-(5-pyrimidinyl) urea (E3)

A mixture of acid (D4, 1.22 g, 9.8 mmol), 5-amino-1-methyl indole (D2, 1.43 g, 9.8 mmol), triethylamine (1.4 ml) and diphenylphosphoryl azide (2.1 ml, 10 mmol) in 1,4-dioxan (100 ml) was heated under reflux overnight. The mixture was evaporated and the residue was dissolved in dichloromethane and washed with 5% citric acid, sat. sodium bicarbonate and water. The organic phase was dried and evaporated and the residue was chromatographed on silica (100 g) eluted with 2–15% methanol/dichloromethane. Combination of appropriate fractions followed by recrystallisation from dichloromethane/methanol gave pure (E3, 0.70 g). mp 210°–213° C.

Found: C, 62.93; H, 4.84; N, 26.06. $C_{14}H_{13}N_5O$ requires C, 62.91; H, 4.90; N, 26.20% NMR ($d_6$-DMSO) δ: 3.76 (3H, s), 6.37 (1H, d, J=3), 7.17 (1H, dd, J=8, 2), 7.29 (1H, d, J=3), 7.37 (1H, d, J=8), 7.69 (1H, d, J=2), 8.78 (2H, s), 8.91 (3H, s).

Example 4

N-(1-Methyl-5-indolyl)-N'-(4-pyridazinyl) urea (E4)

The title compound was prepared by the method of Example 3, using pyridazine-4-carboxylic acid (0.5 g, 4 mmol), aminoindole (D2, 0.59 g, 4 mmol), triethylamine (0.57 ml) and diphenylphosphoryl azide (0.86 ml, 4.1 mmol) in 1,4-dioxan (40 ml). Crude product was chromatographed on silica (75 g) eluted with 5–10% methanol/dichloromethane. The second component was extracted with hot methanol to give an insoluble residue of pure title compound (0.11 g). mp 216°–221° C.

Found: C, 62.17; H, 4.85; N, 25.49 $C_{14}H_{13}N_5O$ requires: C, 62.91; H, 4.90; N, 26.20% NMR ($d_6$-DMSO) δ: 3.78 (3H, s), 6.38 (1H, d, J=3), 7.18 (1H, dd, J=8, 2), 7.30 (1H, d, J=3), 7.38 (1H, d, J=8), 7.70 (1H, d, J=2), 7.81 (1H, dd, J=6, 3), 8.88 (1H, s), 8.91 (1H, d, J=6), 9.20 (1H, d, J=3), 9.29 (1H, s).

Example 5

N-(1-Methyl-5-indolyl)-N'-(3-methyl-5-isothiazolyl) urea (E5)

To a suspension of sodium hydride (80% in oil, 0.99 mg, 3.3 mmol in dry DMF (5 ml) was added 5-amino-3-methylisothiazole hydrochloride (0.15 mg, 1 mmol). After hydrogen evolution had ceased (15 mln), phenyl N-(1-methyl-5-indolyl) carbamate (D3) (0.267 mg, 1 mmol) was added.

The mixture was stirred overnight at room temperature and then evaporated in vacuo. The residue was dissolved in dichloromethane/methanol and the solution was washed with water and brine, dried and evaporated. The crude product was triturated with dichloromethane/petrol and the residue was chromatographed on silica (10 g) eluted with 2% methanol/dichloromethane. Recrystallisation from dichloromethane/petrol gave the title compound (0.10 g). mp. 186°–189° C., 99.6% pure by HPLC.

NMR ($CDCl_3$): δ: 2.32 (3H, s), 3.78 (3H, s), 6.32 (1H, s), 6.44 (1H, d, J=3), 7.08 (1H, d, J=3), 7.18 (1H, dd, J=8, 2), 7.27 (1H, d, J=8), 7.64 (1H, d, J=2). m/z (EI): 286 ($M^+$), 172, 146.

Example 6

N-(1-Methyl-5-indolyl)-N'-(3-methyl-5-isoxazolyl) urea (E6)

The title compound was prepared by the method of Example 5, using 5-amino-3-methylisoxazole (0.098 g, 1 mmol), sodium hydride (0.066 g, 2.2 mmol) and carbamate (D3, 0.267 g, 1 mmol) in dry DMF (5 ml). The crude product was triturated with dichloromethane/petrol, then recrystallised from dichloromethane/methanol/petrol to give the title compound (0.135 g). mp 186°–189° C., 97.5% pure by HPLC.

NMR ($d_6$-DMSO) δ: 2.07 (3H, s), 3.67 (3H, s), 5.84 (1H, s), 6.27 (1H, d, J=3), 7.04 (1H, dd, J=8, 2), 7.18 (1H, d, J=3), 7.26 (1H, d, J=8), 7.58 (1H, d, J=2), 8.53 (1H, s). m/z (EI): 270 ($M^+$), 172

Example 7

N-(1-Methyl-5-indolyl)-N'-(2-(1,3,4-thiadiazolyl)) urea (E7)

A mixture of 2-amino-1,3,4-thiadiazole (1.01 g, 10 mmol), carbamate (D3, 2.67 g, 10 mmol), and N-methylmorpholine (1.2 ml) in DMF (100 ml) was heated at 100°–140° C. overnight, then cooled and evaporated. The residue was dissolved in dichloromethane/methanol and washed with brine and water. The organic phase was dried and evaporated, and the residue was recrystallised from dichloromethane/methanol/petrol to give the title compound (1.54 g). mp 217°–220° C. (decomp.).

Found: C, 52.35; H, 4.07; N, 25.29 $C_{12}H_{11}N_5OS$ requires C, 52.73; H, 4.06; N, 25.62% NMR ($d_6$-DMSO) δ: 3.78 (3H, s), 6.38 (1H, d, J=3), 7.18 (1H, d, J=8), 7.32 (1H, d, J=3), 7.39 (1H, d, J=8), 7.73 (1H, s).

Example 8

N-(1-Methyl-5-indolyl)-N'-(4-(1,2,4-triazolyl)) urea (E8)

To a solution of 1,1'-carbonyldiimidazole (0.27 g) in dichloromethane (10 ml) at 0° C. was added aminomethylindole (D2, 0.22 g, 1.5 mmol) in dichloromethane (10 ml). The mixture was stirred at 0° C. for 15 min, then evaporated and the residue was redissolved in dry DMF (10 ml). 4-Amino-1,2,4-triazole (0.134 g, 1.6 mmol) was added in DMF (2.5 ml) and the mixture was heated at 120°–140° C. for 1 h, then poured into water. The aqueous solution was filtered and evaporated to dryness, and the residue was chromatographed on silica (25 g) eluted with 5–10% methanol/dichloromethane. The second-eluted material was the title compound (0.21 g). mp 202°–206° C.

Found: C, 56.36; H, 4.82; N, 32.65 $C_{12}H_{12}N_6O$ requires: C, 56.24; H, 4.72; N, 32.79% NMR ($d_6$-DMSO) δ: 3.77 (3H, s), 6.35 (1H, d, J=3), 7.18 (1H, dd, J=8, 2), 7.29 (1H, d, J=3), 7.35 (1H, d, J=8), 7.65 (1H, d, J=2).

Example 9

N-(1-Methyl-5-indolyl)-N'-(3-quinolyl)-urea hydrochloride (E9)

A stirred suspension of carbonyl diimidazole (0.34 g, 2.1 mmol) in dry dichloromethane (5 ml) was treated with a solution of 5-amino-1-methylindole (D2, 0.29 g, 2 mmol) in dry dichloromethane (5 ml).

After 0.25 h, the reaction mixture was evaporated to dryness and the residue dissolved in DMF (10 ml). 3-Aminoquinoline (0.32 g 2.2 mmol) was added and the reaction minute heated to 90° C. for 1 h then cooled and added to water (200 ml) with vigorous stirring. The precipitate was filtered, dried and recrystallised from ethanol affording the product as an off-white solid (0.4 g, 66% yield). This was converted into the title compound using HCl in ether. mp 230° C. (from ethanol)

Found: C, 64.42; H, 4.72; N, 15.71. $C_{19}H_{17}N_4OCl$ requires: C, 64.68; H, 4.82; N, 15.87% NMR ($d^6$-DMSO) δ: 3.77 (3H, s), 6.38 (1H, d, J=6), 7.2–7.4 (3H, m), 7.77 (3H, m), 8.1 (2H, m), 8.80 (1H, d, J=3), 9.19 (2H, d, J=12), 9.79 (1H, s).

Example 10

N-(1-Methyl-5-indolyl)-N'-(6-quinolyl)-urea hydrochloride (E10)

A stirred suspension of carbonyl diimidazole (0.34 g, 2.1 mM) in dry dichloromethane (5 ml) was treated with a solution of 5-amino 1-methyl indole (D2, 0.29 g, 2 mM) in dry dichloromethane (5 ml). After 0.25 h, the reaction mixture was evaporated to dryness and the residue dissolved in DMF (10 ml). 6-Aminoquinoline (0.32 g, 2.2 mM) was added and the reaction mixture heated to 90° C. for 1 h then cooled and added to water (200 ml) with vigorous stirring. The precipitate was filtered, dried and recrystallised from ethanol, affording the product as a white solid (0.32 g, 51%). This was converted into the hydrochloride salt (E2) using HCl in ether. mp 208° C. (from ethyl acetate).

NMR ($d^6$-DMSO) δ: 3.77 (3H, s), 6.38 (1H, d, J=3), 7.2–7.4 (3H, m), 7.7–8.2 (4H, m), 8.48 (1H, s), 8.8–9.1 (3H, m), 9.58 (1H, s). m/z (EI): 316 ($M^+$, $C_{19}H_{16}N_4O$)

Example 11

N-(1-Methyl-5-indolyl)-N'-(8-quinolyl) urea (E11)

The title compound was prepared from 8-aminoquinoline, 1,1'-carbonyl diimidazole and 5-amino-1-methyl-indole (D2) using a procedure similar to that described for Example 10, in 31% yield, m.p. 205°–209° C.

NMR ($D_6$-DMSO) δ: 3.76 (3H, s), 6.35 (1H, d, J 3), 7.22 (1H, dd, J 6, 2), 7.27 (1H, d, J 3), 7.36 (1H, d, J 6), 7.5–7.54 (2H, m), 7.60–7.65 (1H, m), 7.8 (1H, s), 8.39 (1H, d, J 6), 8.57 (1H, m), 8.92 (1H, d, J 2), 9.62 (2H, s). Found: $M^+$316 $C_{19}H_{16}N_4O$ requires 316

Example 12

N-(1-Methyl-5-indolyl)-N'-(5-quinolyl) urea (E12)

The title compound was prepared from 5-aminoquinoline, 1, 1'-carbonyl diimidazole and 5-amino-1-methyl-indole (D2) using a procedure similar to that described for Example 10, in 20% yield, m.p 243°–245° C.

NMR ($D_6$-DMSO) δ: 3.76 (3H, s), 6.35 (1H, d, J 2), 7.20 (1H, d, J 6), 7.29 (1H, d, J 2), 7.38 (1H, d, J 6), 7.60-7.65 (1H, m), 7.72 (2H, d, J 3), 7.77 (1H, s), 8.10 (1H, t, J 2), 8.57 (1H, d, J 6) 8.84 (2H, d, J 3), 8.93 (1H, d, J 2) Found: $M^+$ 316 $C_{19}H_{16}N_4O$ requires 316

Example 13

N-(1-Methyl-5-indolyl)-N'-(2-methyl-4-quinolyl) urea hydrochloride (E13)

The title compound was prepared from 4-aminoquinaldine, 1,1'-carbonyl diimidazole and 5-amino-1-methyl-indole (D2) using a procedure similar to that described for Example 10 and then converted to the hydrochloride salt, in 24% overall yield, m.p. 215°–220° C.

NMR ($D_6$-DMSO) δ: 2.80 (3H, s), 3.77 (3H, s), 6.39 (1H, d, J 2), 7.23–7.33 (2H, m), 7.42 (1H, d, J 6), 7.79-7.84 (2H, m), 8.0–8.11 (2H, dd J 6,6), 8.60 (1H, s), 9.08 (1H, d, J 8), 10.8 (1H, s), 10.92 (1H, s), 15.0 (1H, broad s). Found: $M^+$ 330 $C_{20}H_{18}N_4O$ requires 330

Example 14

N-(1-methyl-5-indolyl)-N'-(6-isoquinolyl) urea (E14)

The title compound is prepared using standard methodology as described herein, such as reaction of (D2) with carbonyl diimidazole in a solvent such as dry dichloromethane, and reacting the product with 6-aminoisoquinoline in a solvent such as DMF, with heating.

Example 15

N-(1-Methyl-5-indolyl)-N'-(5-isoquinolyl) urea (E15)

To a solution of carbonyl diimidazole (0.31 g, 2.15 mmol) in dichloromethane (20 ml) was added 5-aminosioquinoline (0.25 g, 1.7 mmol) in dichloromethane (20 ml). After stirring at room temperature for 0.5 h, the solution was evaporated to dryness. The residue was taken up in dimethylformamide (20 ml) and to this solution was added 5-amino-1-methyl-indole (D2) (0.25 g, 1.7 mmol) in dimethylformamide (20 ml). The reaction mixture was heated to 90° C. for 1 h, then cooled and added dropwise to water, with vigorous stirring. The resulting suspension was filtered off, washed with water and dried in vacuo to yield the title compound in 53% yield, m.p. 254°–259° C.

NMR ($D_6$-DMSO) δ: 3.77 (3H, s), 6.37 (1H, d, J 3), 7.19 (1H, dd J 6,2), 7.28 (1H, d, J 3), 7.37 (1H, d, J 8), 7.65.(1H, t, J 6), 7.75–7.8 (2H, m), 7.99 (1H, d, J 6), 8.32 (1H, d, J 6), 8.57 (1H, d, J 6), 8.84 (2H, d, J 8), 9.29 (1H, s). Found: $M^+$ 316 $C_{19}H_{16}N_4O$ requires 316

Example 16

N-(1-Methyl-5-indolyl)-N'-(1-isoquinolyl) urea (E16)

The title compound was prepared from 1-aminoisoquinoline, 1, 1'-carbonyl diimidazole and 5-amino-1-methyl-indole (D2) using a procedure similar to that described for Example 15, in 11% yield, m.p. 230°–233° C.

NMR (CDCl$_3$) δ: 3.81 (3H, s), 6.47 (1H, d, J 2), 7.07 (1H, d, J 3), 7.30 (2H, m), 7.46 (1H, dd J 6,2), 7.61–7.82 (3H, m), 7.97 (1H, s), 8.09–8.16 (3H, m), 12.4 (1H, broad s). Found: $M^+$ 316 $C_{19}H_{16}N_4O$ requires 316

Example 17

N-(1-Methyl-5-indolyl)-N'-(4-isoquinolyl) urea (E17)

The title compound was prepared from 4-aminoisoquinoline, 1,1'-carbonyl diimidazole and 5-amino-1-methyl-indole using a procedure similar to that described for Example 1, and then converted to the hydrochloride salt using hydrogen chloride in ether/ethanol, in 26% overall yield, m.p. 195°–197° C.

NMR (D$_6$-DMSO) δ: 3.77 (3H, s), 6.39 (1H, d, J 2), 7.22 (1H, dd J 6,2), 7.32 (1H, d, J 3), 7.4 (1H, d, J 6), 7.80 (1H, s), 7.94 (1H, t, J 6), 8.13 (1H, t, J 6), 8.39 (1H, d, J 6), 8.55 (1H, d, J 6), 9.24 (1H, s), 9.34 (1H, s), 9.50 ( 2H, d, J 8 ).
Found: M$^+$ 316 C$_{19}$H$_{16}$N$_4$O requires 316

Pharmacological data

[$^3$H]-mesulergine binding to pig choroid plexus membranes in vitro

Evidence from the literature suggests that 5-HT$_{1C}$ antagonists may have a number of therapeutic indications including the treatment of anxiety, migraine, depression, feeding disorders and obsessive compulsion disorders. (Curzon and Kennett, 1990; Fozard and Gray, 1989) and Alzheimer's Disease (Lawlor, 1989, J. Arch. Gen. Psychiat. Vol. 46 p.542).

The affinity of test drugs for the 5-HT$_{1C}$ binding site can be determined by assessing their ability to displace [$^3$H]-mesulergine from 5-HT$_{1C}$ binding sites in pig choroid plexus membranes. The method employed was similar to that of Pazos et al., 1984.

Pooled pig choroid plexi were homogenised in 20 vols of Tris HCl buffer (pH7.4) (containing 4mM CaCl$_2$ and 0.01% ascorbic acid) and centrifuged at 50,000 g for 15 min at 4° C. The supernatant was removed and re-centrifuged. This was repeated a further two times with the incubation of the homogenate (37° C. for 15 min) before the final centrifugation. The final pellet was resuspended in 20 vols of buffer and stored at −70° C. until use.

The tissue suspension (50 ml) was incubated with [$^3$H]-mesulergine (2 nM) in Tris HCl buffer (pH7.4) at 37° C. (containing 0.01% ascorbic acid, 4 mM CaCl$_2$) and 3×10$^{-8}$M spiperone for 30 minutes. Non-specific binding was measured in the presence of mianserin (10$^{-6}$M). Six concentrations of test drug (10$^{-9}$ to 10$^{-4}$M final concentration) were added in a volume of 50 ml. The total assay volume was 500 ml. Incubation was stopped by rapid filtration using a Skatron cell harvester and radioactivity measured by liquid scintillation spectrometry. The IC$_{50}$ values were determined and the pK$_i$ (the negative logarithm of the inhibition constant) calculated from the Cheng Prusoff equation where $$K_i = \frac{IC_{50}}{1 + \frac{C}{Kd}}$$

K$_i$=inhibition constant.
C=concentration of [$^3$H]-mesulergine
Kd=Affinity of mesulergine for 5-HT$_{1C}$ binding sites.
Curzon, G. A. and Keanett, G. A. (1990). TIPS, Vol. 11, 181–182.
Fozard, J. R. and Gray, J. A. (1989). TIPS, Vol. 10, 307–309.
Pazos, A. et al. (1984). Eur. J. Pharmacol., 106, 531–538.
[$^3$H]-Mesulergine binding to rat HT$_{1C}$ clones expressed in 293 cells in vitro The affinity of test drugs for the 5-HT$_{1C}$ binding site can be determined by assessing their ability to displace [$^3$H]-mesulergine from 5-HT$_{1C}$ clones expressed in 293 cells (Julius et al., 1988). The method employed was similar to that of Pazos et al., 1984.

The cells suspension (50 μl) was incubated with [$^3$H]-mesulergine (0.5 nM) in Tris HCl buffer (pH 7.4) at 37° C. for 30 minutes. Non-specific binding was measured in the presence of mianserin (10$^{-6}$M). Ten concentrations of test drug (3×10$^{-9}$ to 10$^{-4}$M final concentration) were added in a volume of 50 μl. The total assay volume was 500 μl. Incubation was stopped by rapid filtration using a Brandel cell harvester and radioactivity measured by scintillation counting. The IC$_{50}$ values were determined using a four parameter logistic program (DeLean 1978) and the pK$_i$ (the negative logarithm of the inhibition constant) calculated from the Cheng+Prusoff equation.
Julius et al. (1988) Science 241, 558–564.
DeLean A, Munson P. J., Rodbaud D. (1978) Am. J. Physiol. 235, E97–E102.

The compounds of examples 3–7, 12, 13, 15 and 17 have pK$_i$ values in the range 5.97 to 8.3.

Reversal of MCPP-induced Hypolocomotion

Administration of m-(chlorophenyl)piperazine (mCPP) to rats induces hypolocomotion (Kennett and Curzon 1988, Luckie et al. 1989) as seen with the related drug 1-(m-trifluoromethylphenyl)piperazine (TFMPP) (Lucki and Frazer 1982, Kennett and Curzon 1988). This effect was blocked by the non specific 5-HT$_{1C}$/5-HT$_2$ receptor antagonists mianserin, cyproheptadine and metergoline and perhaps by mesulergine. It was not blocked by the 5-HT$_2$ receptor antagonists ketanserin and ritanserin at relevant doses (Kennett and Curzon 1991) nor by antagonists of 5-HT$_{1A}$, 5-HT$_{1B}$, 5-HT$_3$, α$_2$ adrenoceptors or dompamine D$_2$ receptors. The effect of mCPP is therefore considered to be mediated by 5-HT$_{1C}$ receptors (Kennett and Curzon 1988) as confirmed by subsequent studies (Lucki et al., 1989). Since mCPP causes hypolocomotion when infused into the cerebral ventricles this effect is probably centrally mediated (Kennett and Curzon 1988).

mCPP-induced hypolocomotion was measured in automated locomotion cages of dimensions 56 cm long×16½× cm wide×25 cm high and made of black perspex. Two photobeams traversed the width of the cages at either end at ground level. Sequential breaking of these beams allowed the measurement of cage transits.

Male Sprague Dawley rats (200–250 g) (Charles River) were housed in groups of six. They were given drugs orally 1 h pretest and 40 mins later mCPP (7 mg/kg i.p.). After a further 20 min they were placed in individual automated cages in groups of four under red light in an adjacent room. After 10 min the test was terminated. Reversal of mCPP-induced hypolocomotion was considered as evidence of in vivo central 5-HT$_{1C}$ receptor antagonist properties.
Kennett, G. A., Curzon, G., (1988). Brit. J. Pharmacol. 94, 137–147.
Kennet G. A., Curzon, G., (1991). Brit. J. Pharmacol. 103, 2016–2020.
Lucki, I., Frazer, A., (1982) Am. Soc. Neurosci. 8(abstr.), 101.
Lucki, I., Ward, M. R., Frazer, A., (1989). J.Pharmacol. Exp. Therap. 249, 155–164.

The compound of Examples 2 and 3 had ID$_{50}$ values of 47.0 and 43.7 mg/kg p.o.

Rat Fundus: 5-HT$_{1C}$-like Receptors

Introduction

The 5-HT receptor in the rat fundic strip (RFS) has been characterised as '5-HT$_{1C}$-like' as its pharmacology is similar, but not identical, to that of rat $5\text{-}HT_{1C}$ receptor dones. Hence this tissue may be used to assess the $5\text{-}HT_{1C}$-like antagonist properties of compounds.

Methods

Whole stomachs were obtained from male CD Rats (Charles River, 250–350 g). Strips of fundus (2 cm×0.5 cm) were cut from the greater curvature and the mucesae carefully removed. Tissues were then further dissected into smaller strips (2 mm×20 mm) which were mounted in organ baths containing oxygensted Tyrodes solution at 37° C. containing indomethacin (3 μM). Preparations were maintained under a resting tension of 0.5 g and exposed to the irreversible MAO inhibitor pargyline (100 μM for 30 minutes followed by washout). Over a 1 h equilibration period, rat fundic strips were challenged with $1\times10^{-8}$M 5-HT at 15 minute intervals until constant responses were obtained. Fifteen minutes later, a complete cumulative concentration-effect curve to the standard agonist 5-HT ($1\times10^{-10}$ upwards) was constructed to determine the individual sensitivity of each preparation. A further concentration-effect curve to either 5-HT, or other agonists was constructed no sooner than 1 h after completion of the previous curve. When necessary tissues were equilibrated with the antagonists over this one hour period. Antagonists affinities are expressed as $pA_2$ estimates.

Results

The compound of Example 5 had a $pA_2$ value of 7.9.

We claim:

1. A compound of formula (I) or a salt thereof:

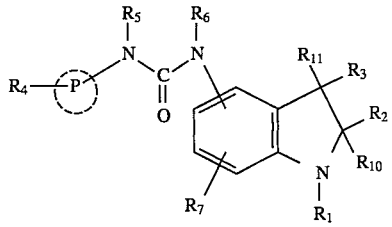

wherein:

P represents a quinoline or isoquinoline residue;

$R_1$ is hydrogen or $C_{1-6}$ alkyl;

$R_2$, $R_3$, $R_{10}$ and $R_{11}$ are independently hydrogen or $C_{1-6}$ alkyl, or $R_{10}$ and $R_{11}$ together form a bond, or $R_2$ and $R_{10}$ or $R_3$ and $R_{11}$ together form a $C_{2-6}$ alkylene chain;

$R_4$ is hydrogen, $C_{1-6}$ alkyl, halogen, $NR_8R_9$, $OR_{12}$ or $COOR_{12}$, where $R_8$, $R_9$ and $R_{12}$ are independently hydrogen or $C_{1-6}$ alkyl;

$R_5$ and $R_6$ are independently hydrogen or $C_{1-6}$ alkyl; and $R_7$ is hydrogen, $C_{1-6}$ alkyl, $C_{1-6}$ alkoxy or halogen; and wherein the urea moiety is attached at the 4-, 5- or 6-position of the indole or indoline ring, provided that P is not pyridyl when $R_{10}$ and $R_{11}$ form a bond.

2. A compound according to claim 1 in which $R_1$ is methyl.

3. A compound according to claim 2 in which $R_2$ and $R_3$ are hydrogen.

4. A compound according to claim 3 in which $R_{10}$ and $R_{11}$ are both hydrogen or $R_{10}$ and $R_{11}$ together form a bond to form an indole structure.

5. A compound according to claim 4 in which $R_4$, $R_5$, $R_6$ and $R_7$ are hydrogen.

6. A compound according to claim 1 in which the urea moiety is attached at the 5-position of the indole or indoline ring.

7. A compound according to claim 1 which is selected from

N-(1-methyl-5-indolyl)-N'-(3-quinolyl)-urea,
N-(1-methyl-5-indolyl)-N'-(6-quinolyl)-urea,
N-(1-methyl-5-indolyl)-N'-(8-quinolyl)urea,
N-(1-methyl-5-indolyl)-N'-(5-quinolyl)urea,
N-(1-methyl-5-indolyl)-N'-(2-methyl-4-quinolyl)urea,
N-(1-methyl-5-indolyl)-N'-(6-Isoquinolyl)urea,
N-(1-methyl-5-indolyl)-N'-(5-isoquinolyl)urea,
N-(1-methyl-5-indolyl)-N'-(1-isoquinolyl)urea,
N-(1-Methyl-5-indolyl)-N'-(4-isoquinolyl)urea,
or a pharmaceutically acceptable salt thereof.

8. A pharmaceutical composition which comprises a compound according to claim 1 and a pharmaceutically acceptable carrier or excipient.

9. A method of antagonizing $5HT_{1C}$ receptor by administering to a subject in need of such treatment an effective amount of a compound according to claim 1.

* * * * *